United States Patent [19]
Lamatsch

[11] Patent Number: 6,087,480
[45] Date of Patent: Jul. 11, 2000

[54] PROCESS FOR PREPARING SPARINGLY SOLUBLE AROMATIC AMINES

[75] Inventor: Bernd Lamatsch, Marly, Switzerland

[73] Assignee: Ciba Specialty Chemcals Corporation, Tarrytown, N.Y.

[21] Appl. No.: 09/212,873

[22] Filed: Dec. 16, 1998

[30] Foreign Application Priority Data

Jan. 13, 1998 [CH] Switzerland ................. 49/98

[51] Int. Cl.⁷ ............... C07C 209/36; C09B 29/036; C09B 29/09; C07D 209/48
[52] U.S. Cl. ............... 534/739; 534/789; 548/306.4; 548/480; 564/416
[58] Field of Search .............. 548/306.4, 480; 564/416; 534/789, 739

[56] References Cited

U.S. PATENT DOCUMENTS

| | | | |
|---|---|---|---|
| 3,397,187 | 8/1968 | Mecum | 528/377 |
| 4,039,522 | 8/1977 | Weaver et al. | 534/789 |
| 4,246,196 | 1/1981 | Arndt et al. | 564/50 |
| 4,473,500 | 9/1984 | Cseh et al. | 534/750 |
| 5,877,340 | 3/1999 | Baumeister et al. | 564/417 X |

FOREIGN PATENT DOCUMENTS

| | | |
|---|---|---|
| 0667376 | 8/1995 | European Pat. Off. . |
| 2200071 | 7/1973 | Germany . |
| 24 60 687 | 7/1975 | Germany . |
| 24 56 308 | 8/1976 | Germany . |
| 25 19 838 | 11/1976 | Germany . |
| 239790 | 10/1986 | Germany . |
| 239791 | 10/1986 | Germany . |
| 1490313 | 11/1977 | United Kingdom . |
| 96/36597 | 11/1996 | WIPO . |

OTHER PUBLICATIONS

Derwent Abstr. 1995–276633 for EP 667376.
Derw. Abst. 76–87174X [47] of DE 25 19 838, 1976.
"Heterogeneous Catalysis for Synthetic Chemist" in Marcel Dekker, Inc. NY,Basle, Hong Kong(1996)pp. 67 & 68 Chapter 5.
Derw. Abst. 75–32496W [20] of DE 24 60 687, 1975.
Derw. Abst. 73–42908U [31] of DE 2200071, 1973.
Derw. Abst. 76–46020X [25] of DE 24 56 308, 1976.
Derw. Abst. 87–037711 [06] of DD 239,791, 1986.
Chem. Abst. 86:55156m of JP 51/110528, 1977.
J. of Amer. Chem. Soc. vol. 29 (1964) p. 3154.

*Primary Examiner*—Fiona T. Powers
*Attorney, Agent, or Firm*—David R. Crichton

[57] ABSTRACT

Preparation of sparingly soluble aromatic amines by catalytic hydrogenation of the corresponding aromatic nitro compounds in the presence of hydrogen, a solvent and a catalyst having a particle size of not less than 0.5 mm, wherein the aromatic nitro compound selected is a compound whose corresponding amine is soluble to an extent of not more than 50% by weight in the solvent used under the reaction conditions of the hydrogenation, and also their use for preparing azo compounds.

14 Claims, No Drawings

PROCESS FOR PREPARING SPARINGLY SOLUBLE AROMATIC AMINES

The present invention relates to an improved process for preparing sparingly soluble aromatic amines by catalytic hydrogenation of the corresponding aromatic nitro compounds in the presence of hydrogen, a catalyst having a particle size of not less than 0.5 mm and a solvent.

DE-A 25 19 838 describes a process for the catalytic hydrogenation of nitro compounds to form the corresponding amino compounds in the downflow mode over a fixed-bed catalyst, where the catalyst has a particle diameter in the range from 0.5 to 3 mm. Both in the examples and in the description, the starting materials and products are completely soluble in the reaction mixture. There are therefore no problems in separating them from the catalyst. Disadvantages of this process are, on the one hand, that catalysts having a particle diameter of greater than 3 mm result, inter alia, in an unsatisfactory conversion and, on the other hand, that the process can only be employed for preparing amino compounds which are soluble in the reaction mixture. There is no indication either in the description or in the examples that the reaction mixture can also be a suspension. This fact is supported by the teachings of R. L. Augustine, "Heterogeneous Catalysis for the Synthetic Chemist", Marcel Dekker, Inc., New York, Basel, Hong Kong 1996, p. 68, according to which it is essential to hydrogenations of nitro compounds to amino compounds that the product is present in solution in order to prevent precipitation of the amino compound on the catalyst and thus deactivation of the catalyst.

WO 96/36597 claims a process for the catalytic hydrogenation of aromatic nitro compounds in solution or in the melt in the presence of, inter alia, a vanadium compound. A disadvantage of this process is that the reaction has to be carried out in solution or in the melt. Although the catalyst can be present in suspension, in the case of a dye which is likewise present in suspension, this would inevitably lead to separation problems during the working up. The entire procedure in WO 96/36597 is directed at soluble products and starting materials, which is consistent with the teachings in "Heterogeneous Catalysis for the Synthetic Chemist", Marcel Dekker, Inc., New York, Basel, Hong Kong 1996, p. 68.

DE-A 24 60 687 describes a process for the catalytic hydrogenation of 1-nitroanthraquinone in an aqueous medium. The reaction product and the catalyst are insoluble in the reaction mixture and can be separated off by filtration. The reaction product thus has to be separated from the catalyst by means of an organic solvent (e.g. dimethylformamide, DMF) in a further step and subsequently has to be freed of solvent. Alternatively, the working up is carried out using concentrated sulfuric acid and the reaction product is precipitated after separating off the catalyst. Both working up methods are cumbersome for commercial use, expensive and involve the risk of contaminating the product, since additional materials (solvent, sulfuric acid) are introduced. In addition, working with DMF or concentrated sulfuric acid is problematical from the point of view of occupational health and safety.

A further method where the reaction product, viz. 1-aminoanthraquinone, is soluble in the reaction mixture is described in DE-A 22 00 071. In this process, the insoluble catalyst is separated off, the reaction mixture is then subjected to an oxidative treatment and the reaction product is subsequently precipitated by addition of a further solvent. A disadvantage here is the use of solvents such as DMF, dimethylacetamide, N-formylpiperidine or N-methylpyrrolidone (NMP). These solvents are problematical from the point of view of occupational health and safety and because of reprocessing.

DE-A 24 56 308 describes a process for preparing an amino compound which is insoluble in the reaction mixture by using a solvent in which the amino compound is insoluble and the nitro compound to be hydrogenated is soluble. Two liquid phases (the solvent and the amino compound together with water) are formed in the reaction and these are separated from one another by means of a separator. The reaction product is thus present in dissolved form, i.e. not a suspension, and the process can only be employed when the reaction product is obtained in the form of a further liquid phase.

In the method described in JP 51/110528, a catalyst such as Pt/C, Pd/C or Rh/C dispersed in an organic phase is used for reducing nitrobenzenes in the presence of hydrogen and an aqueous phase comprising sulfuric acid. The aminobenzenes formed dissolve in the aqueous phase comprising sulfuric acid and can thus be separated from the organic phase containing the catalyst. However, this method cannot be employed for suspensions comprising sparingly soluble amino compounds since the product would always contain some catalyst.

J.Org.Chem. 29 (1964) 3154 describes the preparation of 3-aminophthalimide, where the product has to be extracted from the pulverulent Pd/C catalyst by means of boiling water and, in addition, is obtained in a yield of only 57%.

3- and 4-aminophthalimides can also be prepared from 3- and 4-nitrophthalimides respectively by reduction with reducing agents other than hydrogen. Thus, DD-A 239 791 describes the reduction of 3- and 4-nitrophthalimide using sodium hydrogen sulfite. In the analogous application DD A 239 790, the reduction is carried out using sodium hydrogen sulfide and further reduction using, for example, tin(II) chloride. Furthermore, U.S. Pat. No. 3,397,187 describes the reduction of 4-nitrophthalimide by means of $Na_2S_2O_4$. These processes are either too expensive (use of tin, tin chloride) and/or ecologically dubious and thus finally also uneconomical (use of $Na_2S_2O_4$ and $NaHSO_3$).

It is therefore an object of the present invention to provide a process for preparing sparingly soluble aromatic amines which do not have the abovementioned disadvantages. In particular, the process should be simpler to carry out, particularly with regard to the working up step. The process should also give high yields at simultaneously high concentrations of starting material and product. Furthermore, the solvents used should be easy to handle, present no difficulties in disposal or working up and make it possible to obtain azo compounds more simply and in higher yield.

Accordingly, an improved process has been found for preparing sparingly soluble aromatic amines by catalytic hydrogenation of the corresponding aromatic nitro compounds in the presence of hydrogen, a solvent and a catalyst having a particle size of not less than 0.5 mm, wherein the aromatic nitro compound selected is a compound whose corresponding amine is soluble to an extent of not more than 50% by weight in the solvent used under the reaction conditions of the hydrogenation.

The present invention also provides a process for preparing azo compounds and also provides for the use of the sparingly soluble amines for preparing azo compounds.

The process of the present invention can be carried out either batchwise or continuously. Furthermore, the reaction can be carried out in the downflow mode over a fixed-bed catalyst or can be carried out in a reactor in which the catalyst is present in a rotating basket (spinning basket reactor) or by driving the suspension through the basket by means of propellers (fixed basket reactor).

The aromatic nitro compound used is preferably a nitro compound of the general formula I:

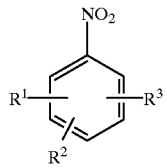

where $R^1$, $R^2$ and $R^3$ are, independently of one another, hydrogen, halogen such as fluorine, chlorine, bromine or iodine, in particular chlorine or bromine, —$NO_2$, —$SO_3H$, —COOH, $C_1$–$C_{18}$alkyl, $C_1$–$C_{18}$alkoxy, $C_2$–$C_{18}$alkenyl, $C_1$–$C_{18}$alkylamino, $C_1$–$C_6$alkylmercapto, $C_1$–$C_{18}$alkoxycarbonyl, $C_1$–$C_{18}$alkylaminocarbonyl, hydroxy, —CN, —$CF_3$, —NH—C(O)—$NH_2$, —NH—C(O)—$C_1$–$C_4$alkyl, preferably —NH—C(O)—$CH_3$, $C_5$–$C_6$cycloalkyl, or a 5- or 6-membered heterocyclic radical, and $R^1$ and $R^2$, if they are in the ortho position relative to one another, together with the ring carbon atoms connected to them may also form a 5- or 6-membered carbocyclic or heterocyclic ring, for example a ring derived from benzene, pyrrolidine, pyrrolidone, imidazolidine, 2-imidazolidone, pyrimidine, pyridone, pyrimidinedione, maleimide, where, according to the invention, the nitro compound I used is one whose corresponding amine II:

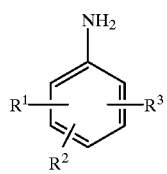

has a solubility in the solvent used of not more than 50% by weight under the reaction conditions of the hydrogenation.

$C_1$–$C_{18}$Alkyl is, for example, methyl, ethyl, n-propyl, isopropyl, n-butyl, sec-butyl, i-butyl, tert-butyl, n-amyl, tert-amyl, hexyl, heptyl, octyl, 2-ethylhexyl, nonyl, decyl, dodecyl, tetradecyl, hexadecyl or octadecyl, preferably $C_1$–$C_8$alkyl such as methyl, ethyl, n-propyl, isopropyl, n-butyl, sec-butyl, i-butyl, tert-butyl, n-amyl, tert-amyl, hexyl, heptyl, octyl, 2-ethylhexyl, particularly preferably $C_1$–$C_4$alkyl such as methyl, ethyl, n-propyl, isopropyl, n-butyl, sec-butyl, i-butyl, tert-butyl.

$C_1$–$C_{18}$Alkoxy is usually, including in $C_1$–$C_{18}$alkoxycarbonyl, for example methoxy, ethoxy, n-propoxy, isopropoxy, butyloxy, hexyloxy, decyloxy, dodecyloxy, hexadecyloxy or octadecyloxy, preferably $C_1$–$C_6$alkoxy such as methoxy, ethoxy, n-propoxy, isopropoxy, butyloxy, hexyloxy.

$C_1$–$C_{18}$Alkylmercapto is, for example, methylmercapto, ethylmercapto, propylmercapto, butylmercapto, hexylmercapto, octylmercapto, decylmercapto, hexadecylmercapto or octadecylmercapto, preferably $C_1$–$C_6$alkylmercapto such as methylmercapto, ethylmercapto, propylmercapto, butylmercapto and hexylmercapto.

$C_1$–$C_{18}$Alkylamino is, including in $C_1$–$C_{18}$alkylaminocarbonyl, for example methylamino, ethylamino, propylamino, hexylamino, decylamino, hexadecylamino or octadecylamino, preferably $C_1$–$C_6$alkylamino such as methylamino, ethylamino, n-propylamino, hexylamino.

$C_5$–$C_6$Cycloalkyl is, for example, cyclopentyl or cyclohexyl, in particular cyclohexyl.

$C_2$–$C_{18}$Alkenyl is, for example, vinyl, n-propenyl, isopropenyl, n-butenyl, sec-butenyl, i-butenyl, n-amenyl, hexenyl, heptenyl, octenyl, 2-ethylhexenyl, nonenyl, decenyl, dodecenyl, tetradecenyl, hexadecenyl or octadecenyl, preferably $C_2$–$C_8$alkenyl such as ethenyl (vinyl), n-propenyl, isopropenyl, n-butenyl, sec-butenyl, i-butenyl, n-amenyl, hexenyl, heptenyl, octenyl, 2-ethylhexenyl, particularly preferably $C_2$–$C_4$-alkenyl such as ethenyl, n-propenyl, isopropenyl, n-butenyl, sec-butenyl, i-butenyl.

The 5- or 6-membered heterocyclic radical can be, for example, imidazolyl, pyrazolyl, thiazolyl, piperazolyl, oxazolyl, morpholinyl, piperidinyl, pyrrolidinyl, pyridyl, pyrimidyl, pyrazinyl, triazinyl, furanyl, pyrrolyl, thiophenyl, quinolyl, isoquinolyl, coumarinyl or pyranyl; this list is to be taken to include condensed heterocycles such as benzoxazolyl, benzothiazolyl and benzimidazolyl.

$R^1$ and $R^2$ can also be selected so that, if they are in the ortho position relative to one another, they can form, together with the ring carbon atoms connected to them, a 5- or 6-membered carbocyclic or heterocyclic ring, for example a ring derived from benzene, pyrrolidine, pyrrolidone, imidazolidine, 2-imidazolidone, maleimide, pyrimidine, pyridone, pyrimidinedione. Accordingly, the nitro compound I used can also be, in particular, an unsubstituted ($R_3$=hydrogen) or substituted compound such as a phthalimidyl, benzimidazolyl, dihydroxyquinazolinyl, quinolonyl, benzoxazolyl, benzoxazolinyl, quinazolinonyl, naphthalene, anthraquinone, benzanthrone or violanthrone derivative or a corresponding nitrated molecule. If this compound is substituted, $R_3$ is preferably hydrogen, halogen, in particular chlorine or bromine, $C_1$–$C_6$alkyl such as methyl, ethyl, n-propyl, isopropyl, n-butyl, sec-butyl, i-butyl, tert-butyl, n-amyl, tert-amyl, hexyl or —$NO_2$, —OH or —$SO_3H$.

The corresponding nitro compounds are known or can be prepared by known methods as are comprehensively described, for example, in Houben-Weyl, Methoden der Organischen Chemie, Volume 10/1 (1971), p. 463 ff and Volume E16 (1992), p. 255 ff.

If the aromatic nitro compound selected is a sparingly soluble compound, a suspension is generally present during the entire reaction time. Otherwise, a suspension is formed only after a sufficient amount of aromatic amine has been produced, so that the reaction mixture is then present as a suspension, at least for most of the time.

In a particularly preferred embodiment of this invention, the aromatic nitro compound used is the phthalimide derivative of the formula III:

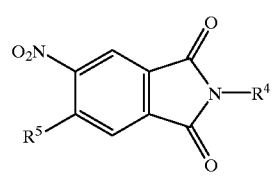

where $R^4$ may be hydrogen or $C_1$–$C_4$alkyl, preferably hydrogen, methyl, ethyl, n-, i-propyl, n-butyl and $R^5$ may be $R^4$, preferably hydrogen, or halogen, in particular chlorine or bromine, or —$NO_2$.

Particular preference is given to 4-nitrophthalimide and 3-nitrophthalimide and also dinitrophenylurea.

The nitro compounds III are known, for example, from Organic Synthesis, Coll. Vol. 2, p. 459 (1943) or can be obtained from the corresponding phthalimides by a method analogous to the method described therein. The corresponding phthalimides are known or can be prepared by methods analogous to known methods (see, for example, Houben-Weyl, Vol.E5, pp. 1118–1125 (1985)).

In a further, particularly preferred embodiment of this invention, the aromatic nitro compound used is a compound of the formula IV:

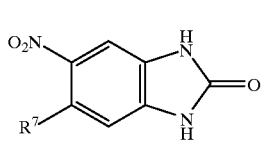

IV where $R^7$ is $R^5$ and —$NHR^6$, $R^6$ being hydrogen or acetyl, and $R^7$ is preferably hydrogen, chlorine, methyl, nitro or —$NHC(O)CH_3$.

The nitro compounds IV are known from, for example, Monatshefte f. Chem., 107 (1976) 1307–1310 or can be prepared by methods analogous to those described therein.

The weight ratio of nitro compound to solvent is usually selected so as to be in the range from 1:5 to 1:100.

It is advantageous to select an excess of hydrogen based on the nitro compound or the number of nitro groups to be hydrogenated, preferably at least 3 mol of hydrogen per mol of nitro compound or per mol of nitro groups to be hydrogenated.

The reaction time naturally depends on various factors such as reaction temperature, reaction pressure, reactivity of the starting material and of the catalyst, etc. It has been found to be advantageous to carry out the reaction until hydrogen absorption or hydrogen consumption is no longer observed. In the case of the reaction parameters indicated here, the reaction time is, for example, in the range from 1 to 60 hours.

The reaction temperature is, as a rule, selected so as to be in the range from 0 to 200° C., preferably from 10 to 100° C.

The reaction pressure is generally selected so as to be in the range from $0.5 \cdot 10^5$ to $10^7$ Pa, the reaction is preferably carried out at atmospheric pressure or in the range from atmospheric pressure to $5 \cdot 10^6$ Pa.

Aromatic amines which are sparingly soluble under the reaction conditions are to be understood as being those aromatic amines of the formula II which, under the reaction conditions, have a solubility in the solvent used of not more than 50% by weight, preferably not more than 20% by weight, particularly preferably not more than 10% by weight, very particularly preferably not more than 2% by weight.

In the case of the known amines, the corresponding solubilities can as a rule be taken from standard reference works. In the case of new amines or known amines whose solubilities are unknown, the corresponding solubilities can be quickly determined by means of simple preliminary experiments, depending essentially on the solvent, concentration and temperature selected. The above condition in respect of the solubility can thus reasonably be expected to be determined.

Examples of particularly preferred aromatic amines which are sparingly soluble in methanol and in water are: 4-aminophthalimide and 3-aminophthalimide (described, for example, in Beilstein, Supplement V, Vol. 22/13, p. 268), 4-amino-N-methylphthalimide, 4-amino-N-ethylphthalimide, 4-amino-N-i-propylphthalimide, diaminoarylureas such as diaminophenylurea (described, for example, in DE-A 2 855 883). For example, the maximum solubility of 4-aminophthalimide in water or methanol is 0.03% by weight: in water, 0.02% by weight of 4-aminophthalimide dissolve at 25° C. and 0.08% by weight at 65° C., and in methanol, 0.26% by weight dissolve at 25° C. (in each case determined at atmospheric pressure; purity of the 4-aminophthalimide at least 99.5% according to HPLC).

Catalysts employed can be supported catalysts or unsupported catalysts, preferably supported catalysts.

Suitable support materials are, as a rule, all customary support materials such as carbon, aluminium oxide, calcium carbonate, zirconium dioxide, $Nb_2O_5$, ZnO, silica ($SiO_2$), $BaSO_4$, aluminium silicate, spinels or titanium dioxide (in the rutile and/or anatase form), preferably carbon, aluminium oxide, $TiO_2$, $SiO_2$ or zirconium dioxide.

Spinels having the composition $A_xB_yO_4$, where A and B are two different metals or semi-metals of main groups I to IV or transition groups I to VIII and x and y are natural numbers which are determined by the mixing ratio and the oxidation numbers of A, B and O. An example is $MgAl_2O_4$. Other spinels are known, for example, from DE-A 2 214 056.

In a preferred embodiment of this invention, use is made of supported catalysts, one dimension of which is in the range from 0.5 to 10 mm, preferably from 1 to 6 mm, particularly preferably from 3.1 to 6 mm. This dimension can be, for example, the length or the diameter and the individual catalyst particles can also have openings. On the basis of observations to date, the shape itself, for example, whether spheres, cylinders, rings, stars, extrudates, granules, flakes or completely irregular, has no effect on the success of the invention.

Catalytically active metals or compounds used can be the customary metals or compounds suitable for the hydrogenation of nitro compounds to give amino compounds. Preference is given to noble metal catalysts alone or as mixed catalysts with other noble metal catalysts and/or base metal catalysts. Particular preference is given to nickel, palladium, platinum, ruthenium, rhodium, iridium or copper. It is also possible to use metal combinations, e.g. as alloys, such as Pd—Pt, Rh—Cu, Pt—Re.

In a particularly preferred embodiment of this invention, use is made of supported catalysts in which nickel, palladium or platinum is applied to carbon, $Al_2O_3$, $SiO_2$, $TiO_2$ or $ZrO_2$ supports. Very particular preference is given to a $Pd/Al_2O_3$ catalyst.

In general, the metal content of supported catalysts is selected so as to be in the range from 0.1 to 20% by weight, preferably from 0.1 to 5% by weight, based on the supported catalyst.

If desired, the catalysts used can comprise additions of metals such as potassium, sodium, lead, copper, bismuth or vanadium or compounds thereof as dopants. In a particularly preferred embodiment of this invention, the additive used is $NH_4VO_3$, $VOSO_4 \cdot 5\ H_2O$, $V_2O_5/SiO_2$ or $NH_4VO_3/C$, which are known, for example, from WO 96/36597.

Accordingly, a preferred embodiment of the process of the invention is one in which the catalyst used comprises, as active component of the catalyst, at least one metal or metal compound comprising elements selected from the group consisting of platinum, palladium, nickel, rhodium, ruthenium and copper and also, if desired, vanadium as dopant.

The catalysts are known and commercially available (e.g. from Degussa), so that information about their preparation is superfluous. For the preparation of suitable catalysts, reference may be made, for example, to DE-A 25 19 838 or WO 96/36597.

In general, from 0.01 to 10 mg of the active catalyst metal or metal alloy is used per gramme of nitro compound.

According to the invention, the hydrogenation is carried out in a solvent. Suitable solvents are preferably water, $C_1$–$C_5$-alkanols such as methanol, ethanol, n-, i-propanol, n-butanol, n-pentanol, preferably methanol, unsubstituted or substituted aliphatic hydrocarbons having from 5 to 16 carbon atoms, e.g. n-pentane, n-hexane, n-heptane, n-octane, n-nonane, n-decane, n-undecane, n-dodecane, n-tridecane, n-tetradecane, n-pentadecane, n-hexadecane, or substituted or unsubstituted aromatic hydrocarbons having from 6 to 14 carbon atoms, e.g. benzene, toluene, xylene, and also ethers, esters or mixtures thereof.

The weight ratio of solvent to nitro compound is generally selected so as to be in the range from 1000:1 to 1:1.

A further preferred embodiment of this invention is a process for preparing an azo compound of the formula V:

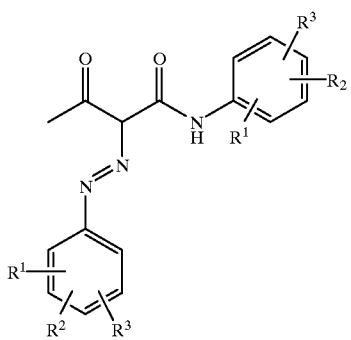

V by diazotisation of an amino compound and subsequent coupling of the diazotised compound with a compound having a CH-active bond in a manner known per se, wherein the amino compound used is a sparingly soluble amine II prepared according to the invention, preferably one prepared from the phthalimide derivative III in which $R^5$ is hydrogen, and the compound having a CH-active bond is an acetoacetarylide of the formula VI:

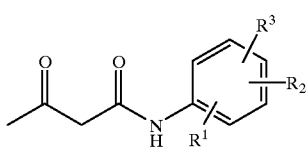

VI

Azo compounds V are known, for example, from EP-A 64 952, EP-A 150 711 and from Hunger/Herbst, Industrielle Organische Pigmente, 2nd edition, in particular chapters 2.3 and 2.8. Particular preference is given to the azo compound V in which $R^1$ is in the para position and is an acetamide group and $R^2$ and $R^3$ are hydrogen.

Acetoacetarylides VI are known, for example, from EP-A 150 711. Particularly preferred acetoacetarylides VI are those, where $R^1$ is in para-position for —NHC(O)CH$_3$, and $R^2$ and $R^3$ are hydrogen.

The diazotisation and the subsequent coupling are generally carried out by methods known per se, as described, for example, in EP-A 150 711.

A further embodiment of this invention is a process for preparing the azo compounds V which comprises (a) hydrogenating a nitro compound of the general formula I:

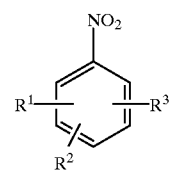

I in a solvent in the presence of a catalyst and hydrogen, where the amount of nitro compound I, based on the solvent used, is selected so that, under the reaction conditions, not more than 50% by weight of the sparingly soluble amine II formed is dissolved in the solvent, and (b) diazotising the resulting sparingly soluble amine II, preferably directly, in the suspension obtained from step (a) in a manner known per se and subsequently coupling it with the acetoacetarylide VI.

The diazotisation is preferably carried out in a manner known per se by treating the sparingly soluble aromatic amino compound II with, for example, sodium nitrite in acid medium. Such a diazotisation is described, for example, in Example 1 of EP-A 64 952.

Furthermore, EP-A 64 952 also comprehensively describes the reaction of a diazotised compound with an acetanilide, i.e. a compound having a CH-active bond. In particular, Example 2 in particular describes the coupling of diazotised 4-aminophthalimide with 4-acetoacetylaminoacetanilide, so that step (b) of the above-mentioned process is comprehensively described in the prior art and further information on this subject is superfluous.

A further, particularly preferred embodiment of this invention is the preparation of azo compounds V, wherein (a) a nitro compound of the formula I, where $R^1$, $R^2$ and $R^3$ are independently of one another hydrogen, chlorine, methyl, trifluoromethyl, carboxyl or nitro, is hydrogenated in a solvent in the presence of a catalyst and hydrogen, where the amount of nitro compound, based on the solvent used, is selected so that, under the reaction conditions, not more than 50% by weight of the sparingly soluble amine II formed is dissolved in the solvent, and (b) the resulting sparingly soluble amine II is diazotised, preferably directly, in the suspension obtained from step (a) in a manner known per se and subsequently coupled with the 5-acetoacetylaminobenzimidazolone VII:

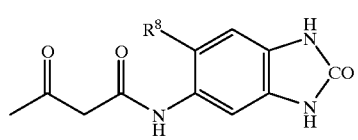

VII where $R^8$ is hydrogen, halogen, preferably chlorine, or $C_1$–$C_4$alkyl, preferably methyl.

The 5-acetoacetylaminobenzimidazolone VII is known (see, for example, Hunger/Herbst, Industrielle Organische Pigmente, 2nd edition, 1995, p. 356), and can be prepared, for example, from the amine IX.

Another particularly preferred embodiment of this invention relates to the preparation of azo compounds V, wherein (a) a nitro compound of the formula IV:

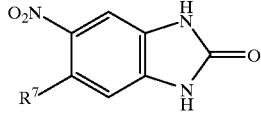

where $R^7$ is preferably hydrogen, chlorine, methyl, nitro or —NHC(O)CH$_3$, is hydrogenated in a solvent in the presence of a catalyst and hydrogen, where the amount of nitro compound, based on the solvent used, is selected so that, under the reaction conditions, not more than 50% by weight of the sparingly soluble amine IX formed is dissolved in the solvent, and (b) the resulting sparingly soluble amine IX:

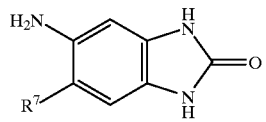

is diazotised, preferably directly, in the suspension obtained from step (a) in a manner known per se and subsequently coupled either with the acetoacetarylide VI:

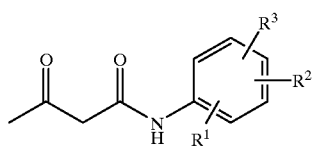

or with barbituric acid:

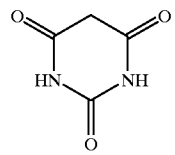

A further, particularly preferred embodiment of this invention relates to the preparation of azo compounds V, wherein (a) a nitro compound of the formula III:

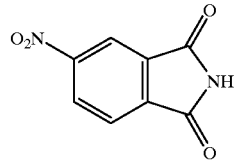

where $R^4$ and $R^5$ are hydrogen, is hydrogenated in a solvent in the presence of a catalyst and hydrogen, where the amount of nitro compound, based on the solvent used, is selected so that, under the reaction coditions, not more than 50% by weight of the sparingly soluble amine of formula VIII formed, where $R^4$ and $R^5$ are hydrogen, is dissolved in the solvent, and (b) the resulting sparingly soluble amine VIII:

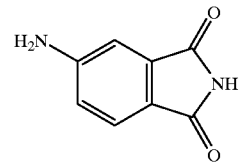

where $R^4$ and $R^5$ are hydrogen, is diazotised, preferably directly, in the suspension obtained from step (a) in a manner known per se and subsequently coupled with the acetoacetarylide VI:

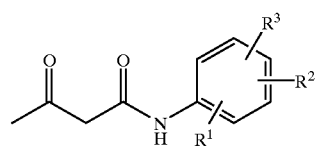

The compounds II prepared according to this invention, in particular the amines of the formula VIII:

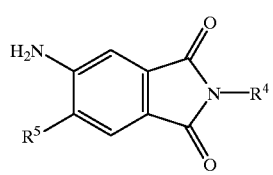

obtained by the process of this invention from the phthalimide derivative III, and the amines of the formula IX:

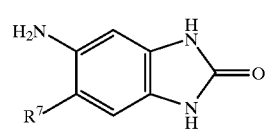

obtained by the process of this invention from the compound IV are important intermediates in the preparation of azo compounds, in particular monoazo compounds, preferably monoazo yellow and monoazo orange pigments, and benzimidazolone pigments.

Accordingly, a further embodiment of this invention is the use of the compounds II prepared according to the invention, in particular the amines VIII and IX, for preparing azo compounds, in particular monoazo compounds and benzimidazolone pigments.

From the amine of formula VIII, for example, phthalimidyl azo dyes are obtainable, in particular disperse azo dyes of the formula X:

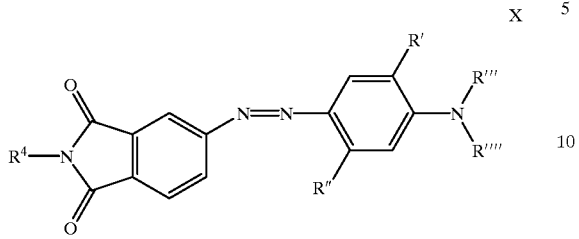

X by the method described in EP-A 667 376 by diazotising the amine VIII and subsequently coupling it with the coupling component:

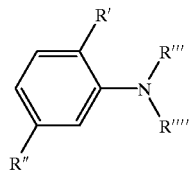

Another embodiment of this invention therefore relates to an improved process for the preparation of phthalimidyl azo dyes of the formula X:

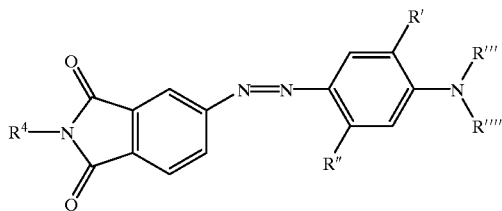

where R' is hydrogen, halogen, $C_1$–$C_4$alkyl; $C_1$–$C_8$alkoxy which is unsubstituted or substituted by halogen, cyano, phenyl, —Y—$C_1$–$C_8$alkyl or —Y-phenyl; R" is hydrogen, $C_1$–$C_2$alkyl, halogen, —NH—$COR^v$ or —O—$SO_2R^{vi}$; R'" is $C_1$–$C_8$alkyl which is unsubstituted or substituted by hydroxy, cyano, vinyl, phenyl, halogen, —X-phenyl or —X—$C_1$–$C_8$alkyl, where —X—$C_1$–$C_8$alkyl may be substituted by halogen or cyano and —X-phenyl may be substituted by $C_1$–$C_4$alkyl, $C_1$–$C_4$alkoxy or halogen; R"" is hydrogen or, independently of R'", may have the meaning of R'", where R'" and R"", together with the linking nitrogen atom, may also be a heterocyclic radical; $R^v$ is $C_1$–$C_4$alkyl which is unsubstituted or substituted by halogen, phenyl, cyano or $C_1$–$C_4$alkoxy; $R^{vi}$ is $C_1$–$C_4$alkyl which is unsubstituted or substituted by halogen, cyano or phenyl, where phenyl is unsubstituted or substituted by $C_1$–$C_4$alkyl, $C_1$–$C_4$alkoxy or halogen; Y is a linking group of formula —O—, —S— or —$SO_2$—, and X is a linking group of formula —O—, —OC(O)—, —OC(O)O—, —C(O)O— or —O—C(O) NH—, which process comprises coupling a coupling component with a diazotised amine in a manner known per se by diazotising the amine VIII and subsequently coupling it with the coupling component:

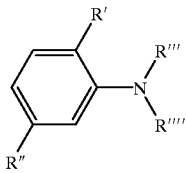

preferably by the method described in EP-A 667 376.

For example, benzimidazolone pigments can also be prepared from the compounds of the formula IX. Depending on the coupling component selected, "yellow pigments" or "red pigments" are obtainable. For example, compound IX with $R^7$=H and diketene or ethyl acetate gives the coupling component 5-acetoacetylaminobenzimidazolone VII which when coupled with a diazotised amino compound II prepared according to the invention leads to usually yellow or orange benzimidazolone pigments. Compound IX, likewise with $R^7$=H and 2-hydroxy-3-naphthoic acid/$PCl_3$ or 2-hydroxy-3-naphthoyl chloride gives an important coupling component of the red series, viz. 5-(2'-hydroxy-3'-naphthoyl)aminobenzimidazolone which when coupled with a diazotised amino compound II prepared according to the invention generally leads to red or brown benzimidazolone pigments (cf. Herbst/Hunger, Industrielle Organische Pigmente, 2nd edition 1995, Chapter 2.8, in particular pages 355–358).

The general preparation of azo compounds such as monoazo compounds, in particular monoazo yellow and orange pigments, diazo compounds, etc., and also the properties and possible uses of the azo compounds prepared according to the invention are comprehensively described in the abovementioned book by Hunger/Herbst, e.g. in Chapter 2.3 and Chapter 2.8.2–2.8.4.

The process of this invention has the advantage that sparingly soluble aromatic amines can be prepared in virtually quantitative yields in an economically utilisable process. Complicated steps and the use of solvents which are dubious from the point of view of occupational health and safety are not necessary. This has made azo compounds, in particular monoazo compounds and benzimidazolone pigments, more readily obtainable.

EXAMPLES

Example 1

0.002 g of ammonium vanadate and 4 g of aluminium oxide granules containing 0.5% by weight of metallic palladium and having a particle size of 3.2 mm (from Acros Organics) are added to a suspension consisting of 250 ml of methanol and 9.6 g of 4-nitrophthalimide. After displacing the air with nitrogen, the latter is replaced by hydrogen at atmospheric pressure and the suspension is stirred at room temperature for 43 hours. During this time, 97.6% of the theoretical amount of hydrogen, based on the nitrophthalimide, is absorbed. The resulting suspension is then sieved through a sieve having a mesh width of 1 mm. The material remaining on the sieve is washed with methanol and the methanol is subsequently removed from the combined methanol phases by means of a rotary evaporator. Drying at 60° C. under reduced pressure (125 mbar) gives 8.1 g (100%) of 4-aminophthalimide.

Example 2

0.002 g of ammonium vanadate and 4 g of aluminium oxide granules containing 0.5% by weight of metallic palladium and having a particle size of 3.2 mm (as in Ex. 1) are added to a suspension consisting of 250 ml of water and 9.6 g of 4-nitrophthalimide. After displacing the air with nitrogen, the latter is replaced by hydrogen at atmospheric pressure and the suspension is stirred at room temperature for 20 hours. During this time, 100.6% of the theoretical amount of hydrogen, based on the nitrophthalimide used, is absorbed. The resulting suspension is then sieved through a sieve having a mesh width of 1 mm. The residue remaining on the sieve is washed with water and the combined aqueous phases are subsequently filtered through a paper filter. Drying at 80° C. under reduced pressure (125 mbar) gives 8.0 g (99%) of 4-aminophthalimide.

Example 3

0.01 g of ammonium vanadate and 20 g of aluminium oxide granules containing 0.5% by weight of metallic palladium and having a particle size of 3.2 mm (as in Ex. 1) are added to a suspension consisting of 250 ml of water and 36 g of 4-nitrophthalimide. After displacing the air with nitrogen, the latter is replaced by hydrogen at atmospheric pressure and the suspension is stirred at room temperature for 20 hours. During this time, 101.2% of the theoretical amount of hydrogen, based on the nitrophthalimide used, is absorbed. The resulting suspension is then sieved through a sieve having a mesh width of 1 mm. The residue remaining on the sieve is washed with 100 ml of water. The resulting yellow suspension, comprising 4-aminophthalimide, is charged with 61 ml of hydrochloric acid (37%) and stirred overnight at room temperature. The greyish yellow suspension obtained is cooled to 5° C. and charged with 46.2 ml of an aqueous 4N sodium nitrite solution. After 30 minutes, the mixture is filtered through a suction filter and the residue is washed with 50 ml of water.

One third of the solution of the diazonium salt obtained above is added dropwise at room temperature to a mixture of 14.5 g of 4-acetaminoacetoacetanilide, 140 ml of water and 7.6 g of a 30% by weight sodium hydroxide solution, with the pH being kept constant by addition of sodium hydroxide solution. The pigment is obtained as a yellow suspension. The mixture is stirred for another three hours at room temperature. The fine pigment suspension is finally filtered through a suction filter. The residue is washed with 1500 ml of water and dried at 60° C. under a pressure of 125 mbar. This gives 23.7 g (94%) of a yellow pigment.

Example 4

0.005 g of ammonium vanadate and 2.5 g 1% by weight of titanium dioxide extrudate containing metallic palladium and having a particle size of 3 mm (from Johnson Matthey) are added to a suspension consisting of 250 ml of water and 10.3 g of 4-nitro-N-methylphthalimide. After displacing the air with nitrogen, the latter is replaced by hydrogen at atmospheric pressure and the suspension is stirred at 63° C. for 75 hours. During this time, 104% of the theoretical amount of hydrogen, based on the 4-nitro-N-methylphthalimide, is absorbed. The resulting suspension is then sieved through a sieve having a mesh width of 1 mm. The material remaining on the sieve is washed with 50 ml of water and the combined aqueous phases are then filtered through a paper filter and washed with 50 ml of water. Drying at 80° C. under reduced pressure (125 mbar) gives 8.3 g (94%) of 4-amino-N-methylphthalimide. The purity determined by high pressure liquid chromatography is 98%.

Example 5

0.001 g of ammonium vanadate and 0.5 g of titanium dioxide extrudate containing 1% by weight of metallic palladium and having a particle size of 3 mm (from Johnson Matthey) are added to a suspension consisting of 50 ml of water and 2.2 g of 4-nitro-N-ethylphthalimide. After displacing the air with nitrogen, the latter is replaced by hydrogen at atmospheric pressure and the suspension is stirred at 65° C. for 42 hours. During this time, 95% of the theoretical amount of hydrogen, based on the 4-nitro-N-ethylphthalimide, is absorbed. The resulting suspension is then sieved through a sieve having a mesh width of 1 mm. The material remaining on the sieve is washed with 50 ml of water and the combined aqueous phases are then filtered through a paper filter and washed with 250 ml of water. Drying at 80° C. under reduced pressure (125 mbar) gives 1.6 g (84%) of 4-amino-N-ethylphthalimide.

Example 6

0.001 g of ammonium vanadate and 0.5 g of titanium dioxide extrudate containing 1% by weight of metallic palladium and having a particle size of 3 mm (from Johnson Matthey) are added to a suspension consisting of 50 ml of water and 2.5 g of 4-nitro-N-butylphthalimide. After displacing the air with nitrogen, the latter is replaced by hydrogen at atmospheric pressure and the suspension is stirred at 65° C. for 68 hours. During this time, 97% of the theoretical amount of hydrogen, based on the 4-nitro-N-butylphthalimide, is absorbed. The resulting suspension is then sieved through a sieve having a mesh width of 1 mm. The material remaining on the sieve is washed with 50 ml of water and the combined aqueous phases are then filtered through a paper filter and washed with 250 ml of water. Drying at 80° C. under reduced pressure (125 mbar) gives 1.7 g (80%) of 4-amino-N-butylphthalimide.

Example 7

0.001 g of ammonium vanadate and 0.5 g of titanium dioxide extrudate containing 1% by weight of metallic palladium and having a particle size of 3 mm (from Johnson Matthey) are added to a suspension consisting of 50 ml of water and 2.3 g of 4-nitro-N-isopropylphthalimide. After displacing the air with nitrogen, the latter is replaced by hydrogen at atmospheric pressure and the suspension is stirred at 65° C. for 71 hours. During this time, 102% of the theoretical amount of hydrogen, based on the 4-nitro-N-isopropylphthalimide, is absorbed. The resulting suspension is then sieved through a sieve having a mesh width of 1 mm. The material remaining on the sieve is washed with 50 ml of water and the combined aqueous phases are then filtered through a paper filter and washed with 1000 ml of water. Drying at 80° C. under reduced pressure (125 mbar) gives 1.2 g (57%) of 4-amino-N-isopropylphthalimide.

Example 8

0.001 g of ammonium vanadate and 0.5 g of titanium dioxide extrudate containing 1% by weight of metallic palladium and having a particle size of 3 mm (from Johnson Matthey) are added to a suspension consisting of 50 ml of water and 1.9 g of 3-nitrophthalimide. After displacing the air with nitrogen, the latter is replaced by hydrogen at atmospheric pressure and the suspension is stirred at 60° C. for 17 hours. During this time, 102% of the theoretical amount of hydrogen, based on the 3-nitrophthalimide, is adsorbed. The resulting suspension is then sieved through a sieve having a mesh width of 1 mm. The material remaining on the sieve is washed with 50 ml of water and the combined aqueous phases are then filtered through a paper filter and washed with 250 ml of water. Drying at 80° C. under reduced pressure (125 mbar) gives 1.2 g (74%) of 3-aminophthalimide.

Example 9

0.001 g of ammonium vanadate and 0.5 g of titanium dioxide extrudate containing 1% by weight of metallic palladium and having a particle size of 3 mm (from Johnson Matthey) are added to a suspension consisting of 50 ml of water and 1.8 g of 5-nitrobenzimidazolone. After displacing the air with nitrogen, the latter is replaced by hydrogen at atmospheric pressure and the suspension is stirred at 60° C. for 34 hours. During this time, 102% of the theoretical amount of hydrogen, based on the 5-nitrobenzimidazolone, is adsorbed. The resulting suspension is then sieved through a sieve having a mesh width of 1 mm. The material remaining on the sieve is washed with 50 ml of water and the combined aqueous phases are then filtered through a paper filter and washed with 250 ml of water. Drying at 80° C. under reduced pressure (125 mbar) gives 1.2 g (79%) of 5-aminobenzimidazolone.

Example 10

0.01 g of ammonium vanadate and 5 g of titanium dioxide extrudate containing 1% by weight of metallic palladium and having a particle size of 3 mm (from Johnson Matthey) are added to a suspension consisting of 500 ml of water and 19.3 g of 5-methyl-6-nitrobenzimidazolone. After displacing the air with nitrogen, the latter is replaced by hydrogen at atmospheric pressure and the suspension is stirred at 65° C. for 78 hours. During this time, 105% of the theoretical amount of hydrogen, based on the 5-methyl-6-nitrobenzimidazolone, is adsorbed. The resulting suspension is then sieved through a sieve having a mesh width of 1 mm. The material remaining on the sieve is washed with 100 ml of water and the combined aqueous phases are then filtered through a paper filter and washed with 50 ml of water. Drying at 80° C. under reduced pressure (125 mbar) gives 15.1 g (93%) of 5-amino-6-methylbenzimidazolone.

Example 11

0.01 g of ammonium vanadate and 8 g of aluminium oxide granules containing 0.5% by weight of metallic platinum and having a particle size of 3.2 mm (from Acros Organics) are added to a suspension consisting of 200 ml of water and 21.4 g of 5-chloro-6-nitrobenzimidazolone. After displacing the air with nitrogen, the latter is replaced by hydrogen at atmospheric pressure and the suspension is stirred at 65° C. At a hydrogen absorption of 85% of theory, another 50 ml of water are added to improve the stirrability and the mixture is then stirred at the same temperature under a hydrogen atmosphere for a total of 98 hours. During this time, 97% of the theoretical amount of hydrogen, based on 5-chloro-6-nitrobenzimidazolone, is absorbed. The resulting suspension is then sieved through a sieve having a mesh width of 1 mm. The material remaining on the sieve is washed with 50 ml of water and the combined aqueous phases are then filtered through a paper filter and washed with 100 ml of water. Drying at 80° C. under reduced pressure (125 mbar) gives 17.5 g (95%) of 5-amino-6-chlorobenzimidazolone. Only traces of 5-aminobenzimidazolone can be found in the NMR.

Example 12

0.002 g of ammonium vanadate and 2 g of titanium dioxide extrudate containing 1% by weight of palladium and having a particle size of 3 mm (from Johnson Matthey) are added to a suspension consisting of 250 ml of water and 13.3 g of N-(4-nitrophenyl)phthalimide. After displacing the air with nitrogen, the latter is replaced by hydrogen at atmospheric pressure and the suspension is stirred at 60° C. At a hydrogen absorption of 40% of theory (after 42 hours), the suspension is transferred to an autoclave together with a catalyst and is then stirred at 100° C. under a hydrogen pressure of 10 bar for another 21 hours. During this time, a total of 115% of the theoretical amount of hydrogen, based on N-(4-nitrophenyl)phthalimide, is absorbed. After cooling to room temperature, the resulting suspension is sieved through a sieve having a mesh width of 1 mm. The material remaining on the sieve is washed with 50 ml of water and the combined aqueous phases are then filtered through a paper filter and washed with 250 ml of water. Drying at 80° C. under reduced pressure (125 mbar) gives 9.4 g (80%) of N-(4-aminophenyl)phthalimide.

What is claimed is:

1. A process for preparing sparingly soluble aromatic amines by catalytic hydrogenation of the corresponding aromatic nitro compounds in the presence of hydrogen, a solvent and a catalyst having a particle size of not less than 0.5 mm, wherein the aromatic nitro compound selected is a compound whose corresponding amine is soluble to an extent of not more than 50% by weight in the solvent used under the reaction conditions of the hydrogenation.

2. A process according to claim 1, wherein the aromatic nitro compound used is a nitro compound of the formula I:

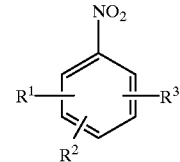

where $R^1$, $R^2$ and $R^3$ are, independently of one another, hydrogen, halogen, $-NO_2$, $-SO_3H$, $-COOH$, $C_1-C_{18}$alkyl, $C_1-C_{18}$alkoxy, $C_1-C_{18}$alkenyl, $C_1-C_{18}$alkylamino, $C_1-C_{18}$alkylmecapto, $C_1-C_{18}$alkoxycarbonyl, $C_1-C_{18}$alkylaminocarbonyl, hydroxy, $-CN$, $-CF_3$, $-NH-C(O)-NH_2$, $-NH-C(O)-C_1-C_4$alkyl, $C_5-C_6$cycloalkyl, or a 5- or 6-membered heterocyclic radical, and $R^1$ and $R^2$, if in the ortho position relative to one another, together with the connected ring carbon atoms, may also form a 5- or 6-membered carbocyclic or heterocyclic ring, where the amount of nitro compound I, based on the solvent used, is selected so that not more than 50% by weight of the sparingly soluble amine of the formula II:

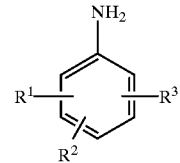

formed under the reaction conditions selected is dissolved in the solvent.

3. A process according to claim 1, wherein not more than 20% by weight of the sparingly soluble amine II:

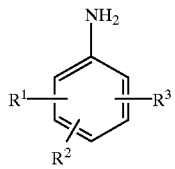

is dissolved in the solvent under the reaction conditions selected.

4. A process according to claim 1, wherein the catalyst used is a supported catalyst or unsupported catalyst in the form of granules, extrudates, cylinders, spheres or flakes.

5. A process according to claim 4, wherein the catalyst comprises as active component at least one metal or a metal compound comprising elements selected from the group consisting of platinum, palladium, nickel, rhodium, ruthenium, iridium and copper, with the active component being capable of being optionally doped.

6. A process according to claim 4, wherein the support used for the supported catalyst is carbon, $Al_2O_3$, $TiO_2$, $SiO_2$, $CaCO_3$, $BaSO_4$, $ZrO_2$, $Nb_2O_5$, ZnO, an aluminosilicate or a spine.

7. A process according to claim 1, wherein the reaction is carried out at a temperature in the range from 0 to 200° C. and/or a pressure in the range from $0.8 \cdot 10^5$ to $10^7$ Pa.

8. A process according to claim 1, wherein the solvent used is water, a $C_1$–$C_5$alkanol, an unsubstituted or substituted aliphatic hydrocarbon having from 5 to 16 carbon atoms or an unsubstituted or substituted aromatic hydrocarbon having from 6 to 14 carbon atoms, an ether, an ester or a mixture thereof.

9. A process for preparing an azo compound of the formula V:

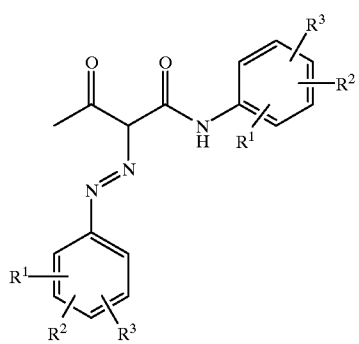

by diazotisation of an amino compound and subsequent coupling of the diazotised compound with a compound having a CH-active bond in a manner known per se, wherein the amino compound used is a sparingly soluble amine II:

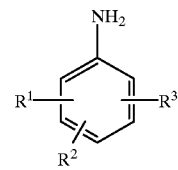

prepared according to claim 1 and the compound having a CH-active bond is an acetoacetarylide of the formula VI:

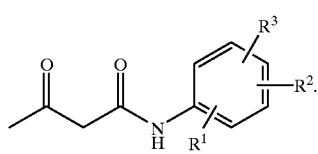

10. A process for preparing an azo compound V according to claim 9, which comprises:

(a) hydrogenating a nitro compound of the formula I:

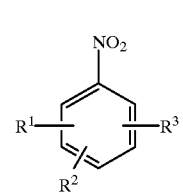

in a solvent in the presence of a catalyst and hydrogen, where the amount of nitro compound I, based on the solvent used, is selected so that, under the reaction conditions, not more than 50% by weight of the sparingly soluble amine formed is dissolved in the solvent, and (b) diazotising the resulting sparingly soluble amine II in a manner known per se and subsequently coupling it with the acetoacetarylide VI.

11. A process for preparing the azo compound V according to claim 10, which comprises (a) hydrogenating a nitro compound of formula I:

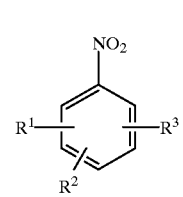

where $R^1$, $R^2$ and $R^3$ are independently of one another hydrogen, chlorine, methyl, trifluoromethyl, carboxyl or nitro, in a solvent in the presence of a catalyst and hydrogen, where the amount of nitro compound, based on the solvent used, is selected so that, under the reaction conditions, not more than 50% by weight of the sparingly soluble amine II formed is dissolved in the solvent, and (b) diazotising the resulting sparingly soluble amine II in the suspension obtained from step (a) in a manner known per se and subsequently coupling it with the 5-acetoacetylaminobenzimidazolone VII:

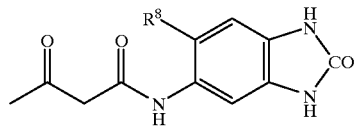

where $R^8$ is hydrogen, halogen, or $C_1$–$C_4$alkyl.

12. A process for preparing an azo compound V according to claim 9, which comprises (a) hydrogenating a nitro compound of the formula IV:

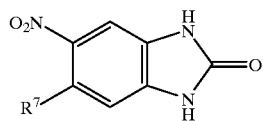

where $R^7$ is hydrogen, $C_1$–$C_4$alkyl, nitro or —$NHR^6$, where $R^6$ is hydrogen or acetyl, in a solvent in the presence of a catalyst and hydrogen, where the amount of nitro compound, based on the solvent, is selected so that, under the reaction conditions, not more than 50% by weight of the sparingly soluble amine IX formed is dissolved in the solvent, and (b) diazotising the resulting sparingly soluble amine IX:

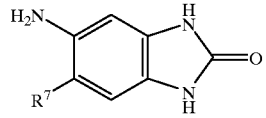

in the suspension obtained from step (a) in a manner known per se and subsequently coupling it either with the acetoacetarylide VI:

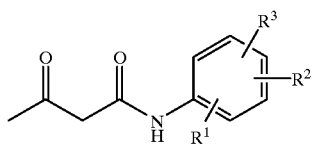

or with barbituric acid:

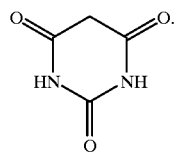

13. A process for preparing an azo compound V according to claim 9, which comprises (a) hydrogenating a nitro compound of the formula III:

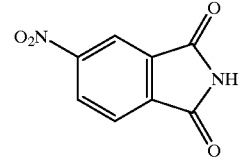

where $R^4$ and $R^5$ are hydrogen, in a solvent in the presence of a catalyst and hydrogen, where the amount of nitro compound, based on the solvent used, is selected so that, under the reaction conditions, not more than 50% by weight of the sparingly soluble amine of formula VIII formed is dissolved in the solvent, and (b) diazotising the resulting sparingly soluble amine VIII:

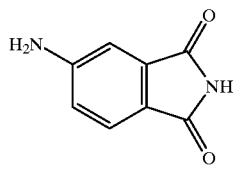

in the suspension obtained from step (a) in a manner known per se and subsequently coupling it with the acetoacetarylide VI:

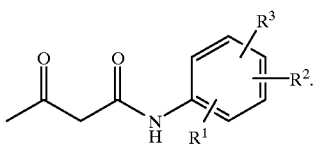

14. A process for preparing a phthalimidyl azo dye of the formula X:

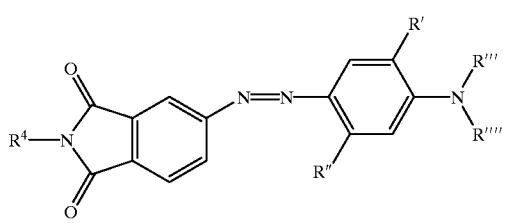

where R' is hydrogen, halogen, $C_1$–$C_4$alkyl; $C_1$–$C_8$alkoxy which is unsubstituted or substituted by halogen, cyano, phenyl, —Y—$C_1$–$C_8$alkyl or —Y-phenyl; R" is hydrogen, $C_1$–$C_2$alkyl, halogen, —NH—$COR^v$ or —O—$SO_2R^{vi}$; R''' is $C_1$–$C_8$alkyl which is unsubstituted or substituted by hydroxy, cyano, vinyl, phenyl, halogen, —X-phenyl or —X—$C_1$–$C_8$alkyl, where —X—$C_1$–$C_8$alkyl may be substituted by halogen or cyano and —X-phenyl may be substituted by $C_1$–$C_4$alkyl, $C_1$–$C_4$alkoxy or halogen; R'''' is hydrogen or, independently of R''', may have the meaning of R''', where R''' and R'''', together with the linking nitrogen atom, may also be a heterocyclic radical; $R^v$ is $C_1$–$C_4$alkyl which is unsubstituted or substituted by halogen, phenyl, cyano or $C_1$–$C_4$alkoxy; $R^{vi}$ is $C_1$–$C_4$alkyl which is unsubstituted or substituted by halogen, cyano or phenyl, where phenyl is unsubstituted or substituted by $C_1$–$C_4$alkyl, $C_1$–$C_4$alkoxy or halogen; Y is a linking group of formula —O—, —S— or —SO$_2$—, and X is a linking group of formula —O—, —OC(O)—, —OC(O)O—, —C(O)O— or —O—C(O)NH—, which process comprises coupling a coupling component with a diazotised amine in a manner known per se by diazotising the amine VIII:
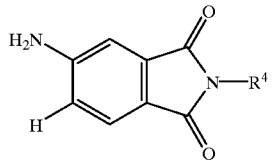
VIII
where R$^4$ is hydrogen or C$_1$–C$_4$alkyl, and subsequently coupling it with the coupling component:
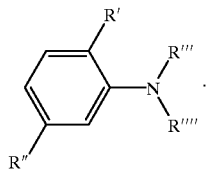
* * * * *